US010722291B2

(12) United States Patent
Rousseau

(10) Patent No.: US 10,722,291 B2
(45) Date of Patent: Jul. 28, 2020

(54) MULTIFUNCTIONAL ELECTROSURGICAL DEVICE

(71) Applicants: Franck Sarrazin, Charce Saint Ellier (FR); Nicolas Rousseau, Omet (FR)

(72) Inventor: Nicolas Rousseau, Omet (FR)

(73) Assignees: Nicolas Rousseau, Omet (FR); Frank Sarrazin, Charce Saint Ellier (FR)

( * ) Notice: Subject to any disclaimer, the term of this patent is extended or adjusted under 35 U.S.C. 154(b) by 225 days.

(21) Appl. No.: 15/507,438

(22) PCT Filed: Jul. 1, 2015

(86) PCT No.: PCT/FR2015/051812
§ 371 (c)(1),
(2) Date: Feb. 28, 2017

(87) PCT Pub. No.: WO2015/193627
PCT Pub. Date: Dec. 23, 2015

(65) Prior Publication Data
US 2017/0281262 A1 Oct. 5, 2017

(30) Foreign Application Priority Data

Sep. 1, 2014 (FR) .................................. 14 58158

(51) Int. Cl.
A61B 18/14 (2006.01)
(52) U.S. Cl.
CPC ...... A61B 18/1442 (2013.01); A61B 18/1402 (2013.01); A61B 2018/1405 (2013.01);
(Continued)
(58) Field of Classification Search
CPC ............ A61B 18/1442; A61B 18/1445; A61B 2018/1445; A61B 2018/1462;
(Continued)

(56) References Cited

U.S. PATENT DOCUMENTS 5,833,689 A 11/1998 Long
5,944,718 A * 8/1999 Austin ............... A61B 18/1445
606/48

(Continued)

FOREIGN PATENT DOCUMENTS

DE 102004031141 A1 1/2006
WO 0203874 A1 1/2002

OTHER PUBLICATIONS

International Search Report for International Application No. PCT/FR2015/051812 dated Oct. 22, 2015, 3 pages.

(Continued)

Primary Examiner — Eun Hwa Kim
Assistant Examiner — Adam Z Minchella
(74) Attorney, Agent, or Firm — TraskBritt

(57) ABSTRACT

The invention concerns a multifunctional electrosurgical device for treating biological tissues comprising a first member and a second member linked by a hinge allowing the members to be moved together and apart from each other; the first member comprising, at the front end of same, a first electrode for forming a first electrical contact with the tissues and the second member comprising, at the front end of same, a second electrode for forming a second electrical contact with the tissues. The first electrode has a concave cross-section, capable of partially housing the second electrode and of making the second electrode protrude from the first electrode when the two members are moved together. The device is remarkable in that the electrodes are configured to allow the formation of the first electrical contact on the outer surface of the first electrode and the formation of the second electrical contact on the protruding part of the second electrode.

9 Claims, 8 Drawing Sheets

(52) U.S. Cl.
CPC ............ *A61B 2018/1412* (2013.01); *A61B 2018/1427* (2013.01); *A61B 2018/1462* (2013.01); *A61B 2018/1495* (2013.01)

(58) Field of Classification Search
CPC .......... A61B 2018/146; A61B 18/1402; A61B 2018/1405; A61B 2018/1412; A61B 2018/1427; A61B 2018/1495
See application file for complete search history.

(56) References Cited

U.S. PATENT DOCUMENTS

| | | | | |
|---|---|---|---|---|
| 6,190,386 | B1* | 2/2001 | Rydell | A61B 18/1442 606/50 |
| 7,367,976 | B2* | 5/2008 | Lawes | A61B 18/1445 606/41 |
| 2001/0037109 | A1* | 11/2001 | Yamauchi | A61B 18/1442 606/48 |
| 2002/0016591 | A1* | 2/2002 | Levine | A61B 18/1442 606/51 |
| 2003/0171747 | A1* | 9/2003 | Kanehira | A61B 17/3201 606/45 |
| 2004/0049185 | A1* | 3/2004 | Latterell | A61B 18/1442 606/48 |
| 2005/0004568 | A1* | 1/2005 | Lawes | A61B 18/14 606/51 |
| 2005/0165444 | A1* | 7/2005 | Hart | A61B 17/12013 606/213 |
| 2006/0184161 | A1* | 8/2006 | Maahs | A61B 18/1492 606/2 |
| 2007/0055226 | A1* | 3/2007 | Garito | A61B 18/1402 606/41 |
| 2007/0179499 | A1* | 8/2007 | Garrison | A61B 18/1445 606/51 |
| 2007/0185487 | A1* | 8/2007 | Hafner | A61B 18/1442 606/45 |
| 2007/0276363 | A1* | 11/2007 | Patton | A61B 18/1442 606/51 |
| 2013/0066317 | A1* | 3/2013 | Evans | A61B 18/042 606/48 |
| 2014/0148801 | A1* | 5/2014 | Asher | A61B 17/30 606/33 |
| 2015/0025530 | A1* | 1/2015 | Zada | A61B 18/08 606/40 |

OTHER PUBLICATIONS

International Written Opinion for International Application No. PCT/FR2015/051812 dated Oct. 22, 2015, 6 pages.

European Office Action dated Feb. 21, 2018 for European Application No. 15753089, 14 pages with English translation.

* cited by examiner

MULTIFUNCTIONAL ELECTROSURGICAL DEVICE

CROSS-REFERENCE TO RELATED APPLICATIONS

This application is a national phase entry under 35 U.S.C. § 371 of International Patent Application PCT/FR2015/051812, filed Jul. 1, 2015, designating the United States of America and published as International Patent Publication WO 2015/193627 A1 on Dec. 23, 2015, which claims the benefit under Article 8 of the Patent Cooperation Treaty to French Patent Application Serial No. 1458158, filed Sep. 1, 2014.

TECHNICAL FIELD

The present application relates to a multifunctional electrosurgical device.

BACKGROUND

In the prior art, electrosurgical devices for performing operations of incision or cauterizing of tissues of a patient are known.

These are generally devices guided by hand by a surgeon, making it possible to apply to the tissues a high-frequency energy coming from a generator by means of a first electrode. The generator makes it possible to choose the energy level and the waveform suited to the surgery. In single-pole configuration, a return electrode is positioned on the patient. In dual-pole configuration, the device is provided with a secondary electrode to make it possible to circulate the energy in the tissues between the two electrodes.

The incision and/or cauterizing operations are produced by the heat able to develop at the tissues where the energy is concentrated and/or circulates.

According to the energy density delivered by the first electrode, an incision or cauterizing effect is obtained. In general terms, the incision is made when the energy density is sufficient to destroy the cells forming the tissues. The energy level and the waveform supplied by the generator can be adjusted by the surgeon by means of control switches disposed, for example, on the device or on the floor or by acting directly on the generator.

Known devices of the prior art make it possible to operate in a first so-called "pressure" mode. In this mode, the electrosurgical device is applied in guided contact on the tissue, that is to say, by maintaining the contact between the electrode or electrodes and the tissues during the guided movement of the device by the surgeon. U.S. Pat. No. 5,833,689 presents such a device making it possible, according to the energy level and/or the waveform delivered by the generator, to incise or cauterize the tissues treated.

Other known devices of the prior art make it possible to operate in a second so-called "gripping" mode. In this mode, the tissues are gripped between the two electrodes of the device, which is then in the form of a clamp or scissors. U.S. Patent Publications 2014/0148801 and 2004/0049185 present such a device, which makes it possible, according to the energy level and/or the waveform delivered by the generator, to incise or cauterize the tissues being gripped.

During an operation, the surgeon generally has available a multiplicity of such electrosurgical devices making it possible, according to requirements, to operate in a pressure mode or in a gripping mode. The repeated changes of electrosurgical devices to change from one mode to the other, and repeated adjustment of the energy delivered by the generator for switching the device between incision and cauterizing, constitute significant constraints for the surgeon. These constraints, in fact, make it necessary to interrupt the operation regularly, which is a source of risks and inefficiency for its correct performance and, in addition, involve expensive hardware and human resources. Moreover, they lead to repeatedly introducing and extracting the electrosurgical device suitable for accessing the tissues and treating them, which may form an additional source of increased difficulties or risks.

BRIEF SUMMARY

One object of the disclosure is to propose a multifunctional electrosurgical device for treating tissues in a plurality of different operating modes and, in particular, in pressure and in gripping.

Another object of the disclosure is to propose a multifunctional electrosurgical device that can treat tissues in incision and in cauterizing without necessarily adjusting the energy level and/or the waveform delivered by the generator during the surgery.

For the purpose of achieving at least one of these aims, the subject matter of the disclosure proposes a multifunctional electrosurgical device for treating biological tissues comprising a first member and a second member connected by an articulation pivot, making it possible to move the members closer to and further away from each other; the first member comprising at its front end a first electrode for forming a first electrical contact with the tissues and the second member comprising at its front end a second electrode for forming a second electrical contact with the tissues. The first electrode has a concave cross-section able to at least partially house the second electrode and to make the second electrode protrude from the first electrode when the two members are moved closer together.

The device according to the disclosure is remarkable in that the electrodes are configured so as to allow the formation of the first electrical contact on the external surface of the first electrode and the formation of the first electrical contact on the external surface of the first electrode and the formation of the second electrical contact on the projecting part of the second electrode.

Thus, it is possible to treat the tissues in gripping by seizing them between each of the electrodes of the articulated members.

In addition, the concave form of the first electrode and the projecting position of the second electrode vis-à-vis the first electrode when the two members are brought together, makes it possible to establish and maintain electrical contact between the external surface of the first electrode and the tissues and between the projecting part of the second electrode and the tissues during the guided movement of the device, and thus to treat the tissues under pressure.

According to other advantageous and non-limitative features of the disclosure, taken alone or in combination:
 the end of the second electrode projects in length beyond the end of the first electrode when the two members are brought together;
 the second electrode is not entirely housed, over its height, inside the concavity of the first electrode when the two members are brought together, so that the second electrode projects in height beyond this concavity;
 the longitudinal axes of the electrodes are not parallel to each other when the two members are brought together;

the second electrode has an end in the form of a blade or in the form of a needle;

the second electrode has an end in the form of a blade and is oriented so that its edge is housed in the first electrode having a concave cross-section when the two members are brought together;

the second member is provided with means making it possible to rotate the second electrode about an axis substantially defined by the longitudinal axis of the second member;

the means for rotating the second electrode comprise a rosette;

the device is provided with means for guiding the first and second members (2, 3); and the electrodes are connected to gripping elements interchangeably.

BRIEF DESCRIPTION OF THE DRAWINGS

The disclosure will be understood better in the light of the following description of particular non-limitative embodiments with reference to the accompanying figures, among which.

DETAILED DESCRIPTION

The term "incision" used in the following detailed description designates the making of a cut or slit of any dimension and depth in biological tissues. It may be a cut or a slit performed during a dissection operation. The incision may comprise the coagulation of the incised tissues.

As for the term "cauterizing," this designates in this description the effects of any surface treatment of biological tissues obtained by the application of heat. This application may lead to phenomena of coagulation, desiccation, hemostasis or any other phenomenon leading to the closure of blood vessels.

"Treatment" means indifferently an incision, a cauterization or any other effect that the device according to the disclosure could cause on the tissues to which it is applied.

Finally, the term "tissues" designates any set of biological cells.

Figure 1:
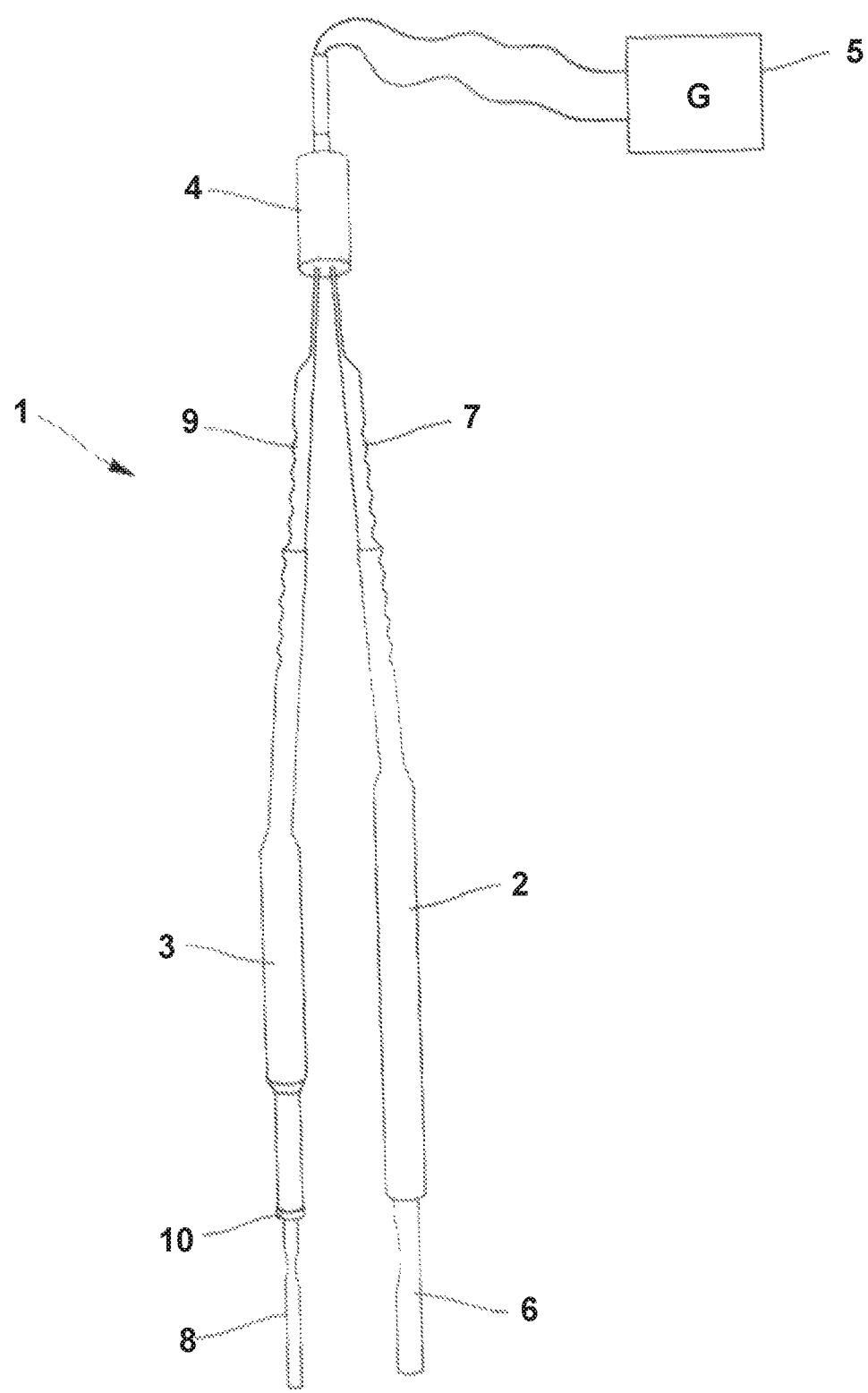
FIG. 1 shows an overall view of an embodiment of the multifunctional electrosurgical device according to the disclosure.
Figure 2:
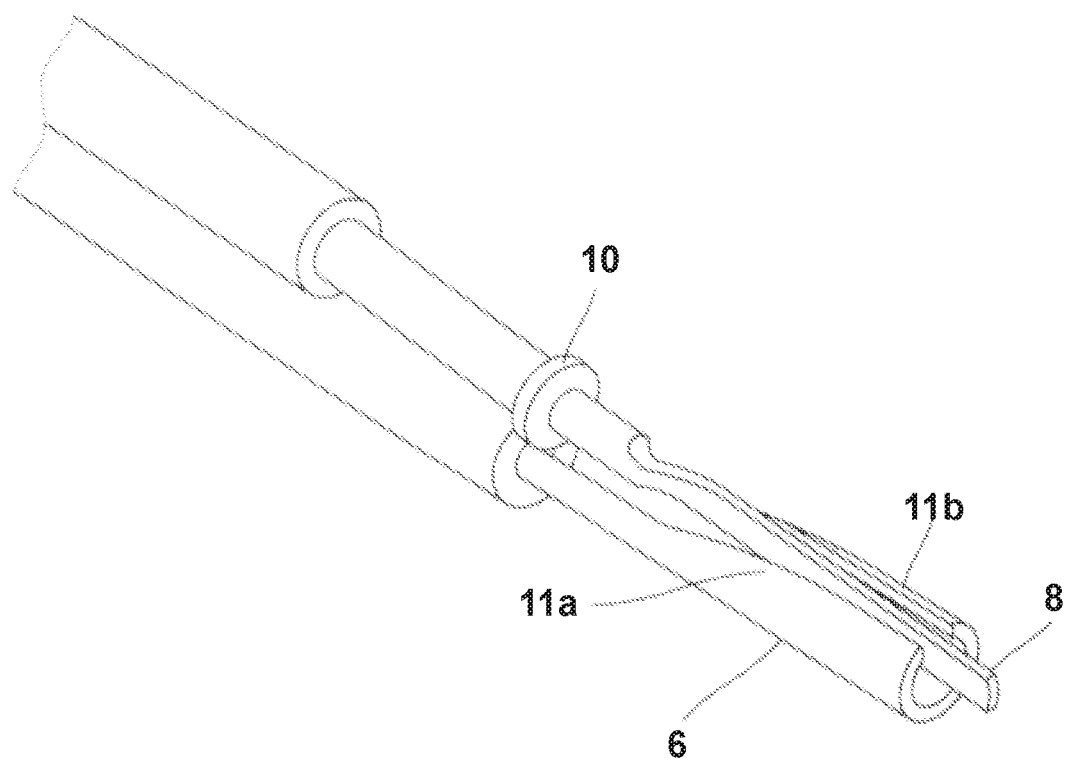
FIG. 2 shows a close-up view of the electrodes of the multifunctional electrosurgical device in a preferred embodiment.

FIG. 1 shows an overall view of an embodiment of the multifunctional electrosurgical device 1 according to the disclosure. It comprises a first member 2 and a second member 3 connected to each other by an articulation pivot 4, making it possible to move the members 2, 3 closer or further away from each other.

In the preferred configuration of the multifunctional electrosurgical device 1 shown in FIG. 1, the articulation pivot 4 is disposed at the rear end of each member 2, 3 in order to form a clamp. Other configurations are possible and, in particular, the articulation pivot 4 may be placed in the central part of the members 2, 3 in order to form scissors.

The members 2, 3 are kept distant from each other when no pressure is exerted on them by, for example, holding means incorporated in the articulation pivot 4.

The multifunctional electrosurgical device 1 is electrically connected to a generator 5, known, per se, to be able to generate the high-frequency signals leading to the performance of the treatments, such as an incision or a cauterizing. It may be a current generator.

The first member 2 of the multifunctional electrosurgical device 1 consists, at its front end, of a first electrode 6 connected to a gripping element 7. This first electrode 6 is in electrical connection with the generator 5 by means of a current cable, for example, along the gripping element 7 or incorporated therein.

Similarly, the second member 3 consists, at its front end, of a second electrode 8 connected to a gripping element 9. This second electrode 8 is in electrical connection with the generator 5 through means similar to those described in relation to the first member 2.

The electrode 6 and the gripping element 7 and, respectively, the electrode 8 and the gripping element 9, may be secured to each other or assembled permanently. In this case, the multifunctional electrosurgical device 1 is for single use. The electrodes 6, 8 and the corresponding gripping elements 7, 9 may then be formed by a single conductive element, for example, metal, providing the electrical connection between the electrodes 6, 8 and the generator 5. The part of the metal element corresponding to the gripping elements 7, 9 is provided with an electrically insulating sheath to enable the device 1 to be handled during functioning thereof.

Advantageously, the electrodes 6, 8 are connected interchangeably to the gripping elements 7, 9; for example, by means of housings formed in the gripping elements 7, 9 in which the rear ends of the electrodes 6, 8 can be inserted and establish the electrical connection with the generator 5. In the case of interchangeable electrodes, only these electrodes have to be replaced regularly, which constitutes an appreciable economic advantage. In some cases, it may be advantageous to sterilize the electrodes 6, 8 between each operation to enable them to be reused.

The electrodes 6, 8 consist of, or comprise, an electrically conductive material. It may, for example, be stainless steel. Stainless steel may be polished in places in order to prevent the tissues from sticking to the electrodes 6, 8 during treatment.

The gripping elements 7, 9 for their part consist of insulating materials, such as, for example, polyetheretherketone (also referred to as PEEK), enabling them to be handled without risk by the surgeon during an operation.

As indicated previously, the gripping elements 7, 9 may be provided with conduits to house the cables providing the connection between each of the electrodes 6, 8 and the generator 5.

Alternatively, the gripping elements 7, 9 may be formed by an electrically conductive core, for example, a metal, provided with an electrically insulating sheath.

According to the disclosure, and as particularly notable in FIGS. 2, 3, 4 and 6:

the first electrode 6, associated with the first member 2, has a concave cross-section able to partly house the second electrode 8 when the two members 2, 3 are brought together by rotation about the articulation pivot 4; the first electrode 6, therefore, defines a concave housing having an internal surface. The first electrode 6 has external flanks 11a, 11b defining an external surface, complementary to the internal surface;

the second electrode 8 projects from the first electrode 6 when the two members 2, 3 are brought together, to allow contact of each electrode with the tissues.

The electrodes are configured so as to allow the formation of a first electrical contact on the external surface of the first electrode 6 and the formation of a second electrical contact on the projecting part of the second electrode 8.

This arrangement is facilitated by configuring the device 1 so that the longitudinal axes of the electrodes 6, 8 are not parallel to each other in a working configuration, when the two members 2, 3 are brought together. For example, and as is visible in FIG. 1, the device 1 may be configured so that the two electrodes 6, 8 have longitudinal axes parallel to each other in the idle position, that is to say, when no pressure is applied to one of the members 2, 3. This may be obtained by giving a curved form to the gripping elements 7, 9 along their longitudinal axes, and in a direction of curvature opposite to each other.

Thus, in a first configuration, the end of the second electrode 8 may project in length beyond the end of the first electrode 6 and thus form the projecting part. The projection in length may be between 0.01 and 20 mm.

In a second configuration, alternative or complementary to the first configuration, the second electrode 8 is not entirely housed in the concavity of the first electrode 6 and projects in height beyond the flanks 11a, 11b of the concavity of the first electrode 6, in order to form the projecting part. This configuration, therefore, also makes it possible to make the second electrode 8 project beyond the first electrode 6 when the two members 2, 3 are brought together, in order to enable each electrode to come into contact with the tissues. This arrangement is particularly visible in FIG. 4, and allows a linear contact of the electrode 8 with the tissues, as will be disclosed hereinafter. The projection in height may be between 0.01 and 20 mm.

The concave form of the first electrode 6 has the advantage of enabling the electrodes 6, 8 to be brought together to a very short distance and to facilitate in this way the circulation of energy through the tissues. In addition, the flanks 11a, 11b of the first electrode 6 form extensive electrical contact surfaces with the tissues, which can be taken advantage of when the device is used, as will be detailed hereinafter. Consequently, the surface area of the first contact formed between the first electrode 6 and the tissues may be more extensive than the second surface area of contact formed between the second electrode 8 and the tissues. In this case, the energy density is more intense at the second electrode 8, which makes it active during treatment, than at the first electrode 6, which makes it passive during the treatment.

In a variant, the end of the first electrode may be beveled and the beveled section may form and/or also participate in the surface of the first contact with the tissues.

Figure 3:
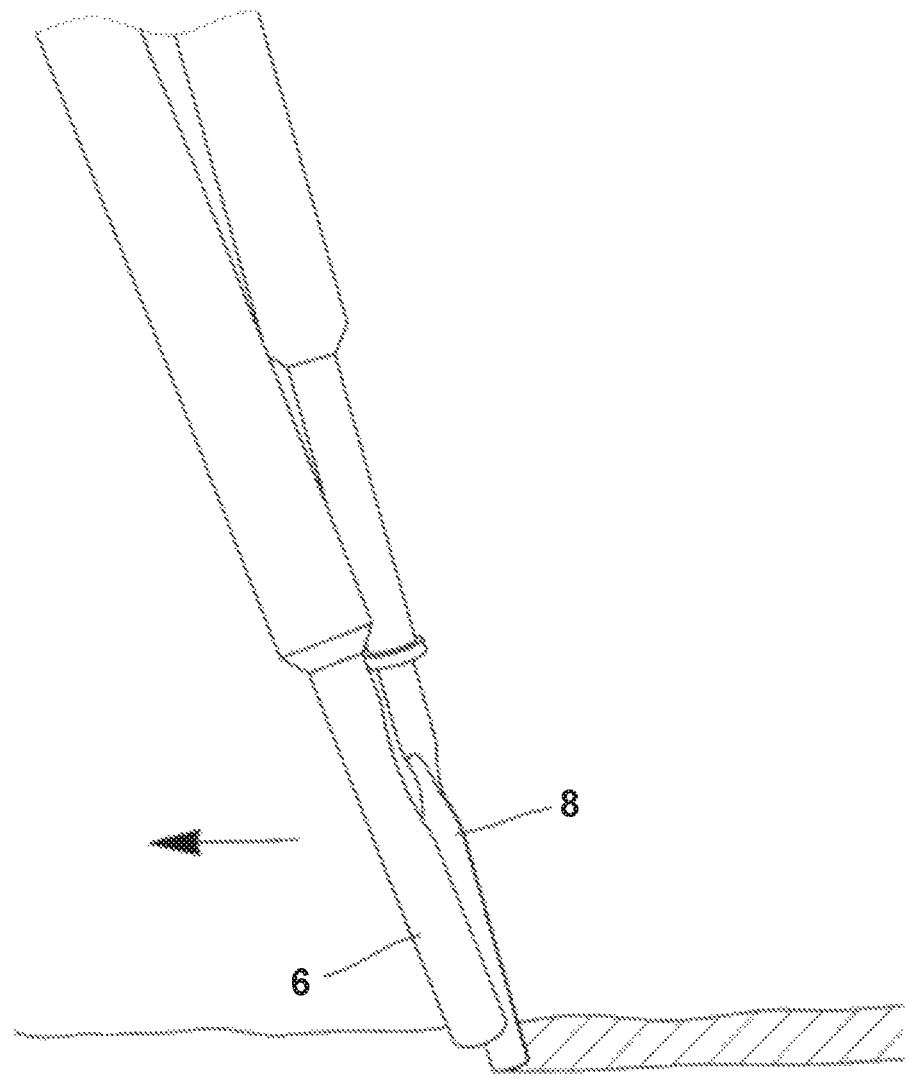
FIG. 3 shows the arrangement of the device of the disclosure for pressure incision treatment.
Figure 4:
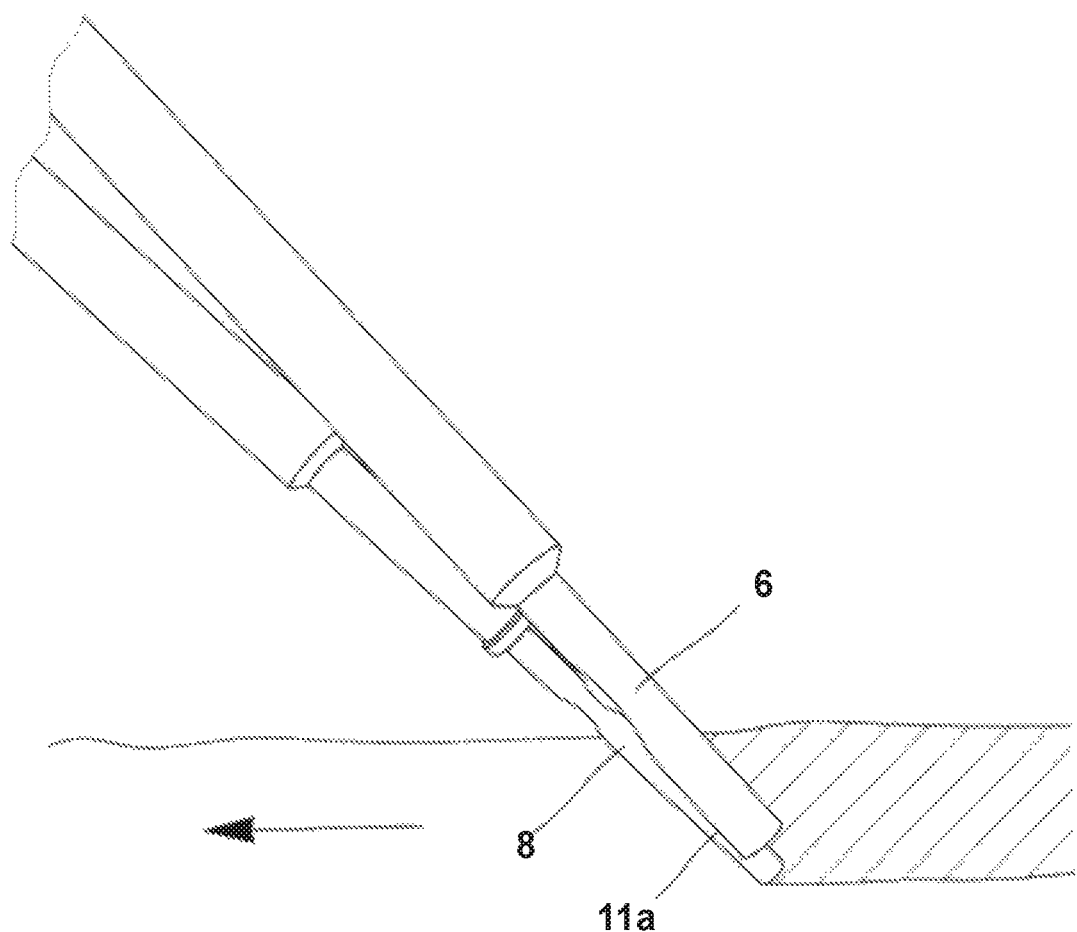
FIG. 4 shows an alternative arrangement of the device of the disclosure for pressure incision treatment.
Figure 6:
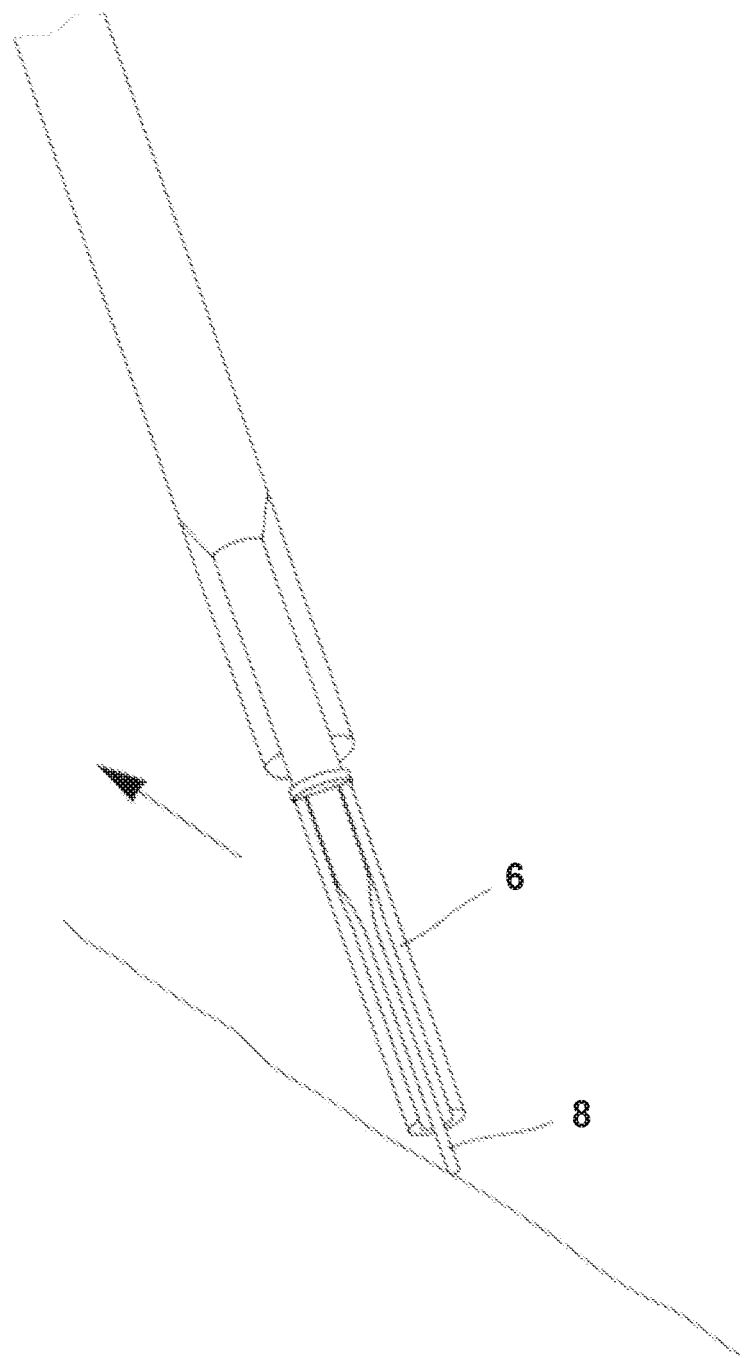
FIG. 6 shows the arrangement of the device of the disclosure for pressure cauterizing treatment.

Thus, the multifunctional electrosurgical device 1 can be employed in a first pressure mode. This first mode is obtained by exerting a pressure on the gripping elements 7, 9 so as to bring the members 2, 3 together by rotational movement about the articulation pivot 4. As can be seen in FIGS. 3, 4 and 6, the projecting arrangement of the second electrode 8 vis-à-vis the first electrode 6 makes it possible to form the respective electrical contacts with the tissues by adjusting the working angle of the device 1. In this method of use, the first electrical contact is formed on the external surface of the first electrode 6 and the second electrical contact is formed on the projecting part of the second electrode 8.

The working angle of the device corresponds to the angle existing between its longitudinal axis and the working plane formed by the plane tangent to the tissues being treated. According to the pressure exerted by the surgeon on the gripping members 7, 9, it is possible to adjust the approach of the second electrode 8 vis-à-vis the first electrode 6 and, consequently, to adjust the working angle of the device 1. In this way, the surgeon can choose the working angle that is most propitious to the treatment to be undertaken.

Figure 5:
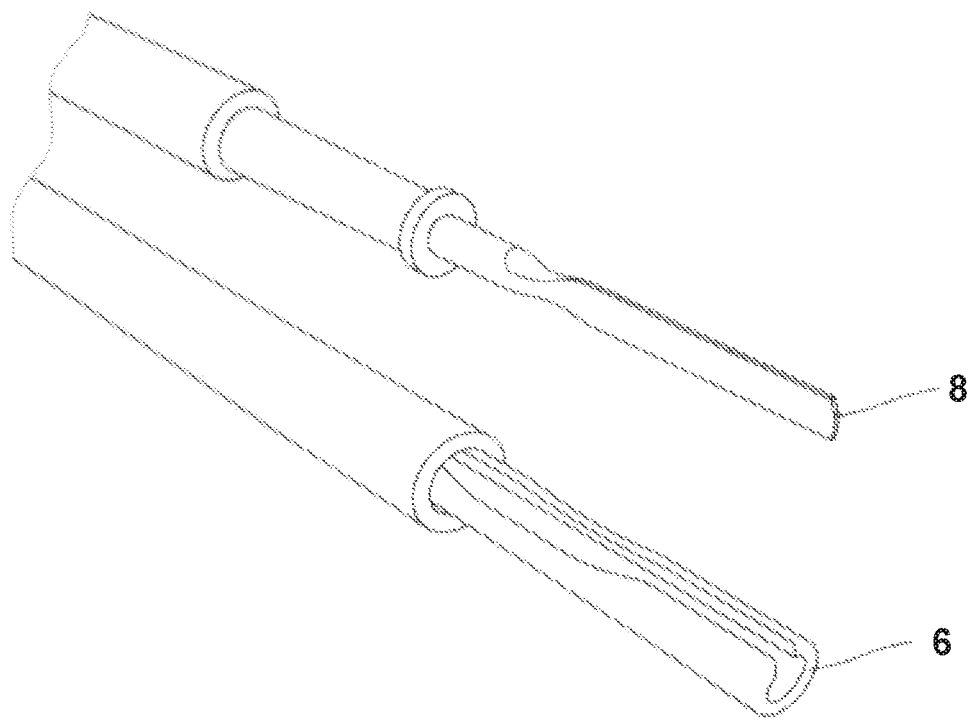
FIG. 5 shows the arrangement of the device of the disclosure for gripping incision treatment.

The multifunctional electrosurgical device 1 according to the disclosure may also be employed in a second gripping mode shown in FIG. 5, the articulation pivot 4 making it possible to use the members 2, 3 to grip the tissues between the electrodes 6, 8 and to form the electrical contacts between these electrodes 6, 8 and the tissues with a view to treating them.

It is thus possible to have available a single device for treating the biological tissues in pressure and in gripping during surgery.

In a particular configuration, the concave cross-section of the first electrode 6 is a portion of a circle. It is thus possible to form large contact surfaces on the flanks 11a, 11b of this electrode with a minimum size of the electrode 6.

The second electrode 8 may have any form, for example, a needle shape, but, in the preferred implementation of the device 1 of the disclosure, the second electrode 8 of the second member 3 has an end in blade form. "Blade form" means in the form of a flat thin band.

Thus, depending on the orientation of the device 1 and/or of the second electrode 8, it is possible to form the second electrical contact between the second electrode 8 and the tissues, either on the flat or on the edge of the second electrode 8 in blade form. It is thus possible to vary the extent of the contact surface and consequently the energy density delivered and/or circulating at the second electrical contact and in its vicinity without needing to adjust the energy level and the waveform delivered by the generator 5. As will be detailed hereinafter, the device 1 can treat the tissues in incision and in cauterizing.

It is not necessary for the second electrode 8 to have a sharp edge. This is because the incision of the tissues is obtained by the heating produced by the circulation of energy with sufficient density therein rather than by a shearing effect.

When the two members 2, 3 are brought together by rotation about the articulation pivot 4, it is preferable for the two electrodes 6, 8 not to come into direct electrical contact. This absence of direct electrical contact may be obtained by avoiding bringing the two members too close together when the device is used. In gripping mode, the absence of direct electrical contact is obtained by the presence of the tissues between the electrodes 6, 8. It may also be obtained by adjusting the dimensions and positions of one or the other, or both, of the electrodes 6, 8, so that when the two members 7, 9 come into abutment, the two electrodes 6, 8 do not contact each other. To this end, one of the members 2, 3 may have a stop device, such as, for example, a collar 10 at the end of one of the gripping elements 7, 9.

Alternatively or in addition to these various means, because the surface of the first electrode 6 and, in particular, the internal surface of the housing concavity, are liable to come into contact with the second electrode 8 when the two members 2, 3 are brought closer together, the first and second electrodes 6, 8 may be provided with an electrically insulating cladding.

Thus, and by way of example, the first electrode 6 may be formed from stainless steel, the internal surface of the concavity of this electrode 6 being provided with an electrically insulating cladding.

The device may also be provided with means for guiding the first and second members when they are brought closer together. These means make it particularly possible to position a part at least of the second electrode 8 with precision in the concavity of the first electrode 6. It may be a case, for example, of a lug positioned on one of the members 2, 3 sliding in an opening formed opposite the lug in the other member, when the two members 2, 3 are brought closer together.

Advantageously, the second member 3 has means making it possible to rotate the second electrode 8 about an axis substantially defined by the longitudinal axis of the second member 3. These means may be used by the surgeon so that he can change from a configuration where the flat of the second electrode 8 is oriented so as to electrically contact the tissues to a configuration where the edge of the second electrode 8 is oriented so as to electrically contact the tissues. It may be a case of a lug formed on the second electrode 8, making it possible to rotate, and preferentially through 90°, the second electrode 8 in the housing of the gripping element 9 in which it is inserted.

Figure 8:
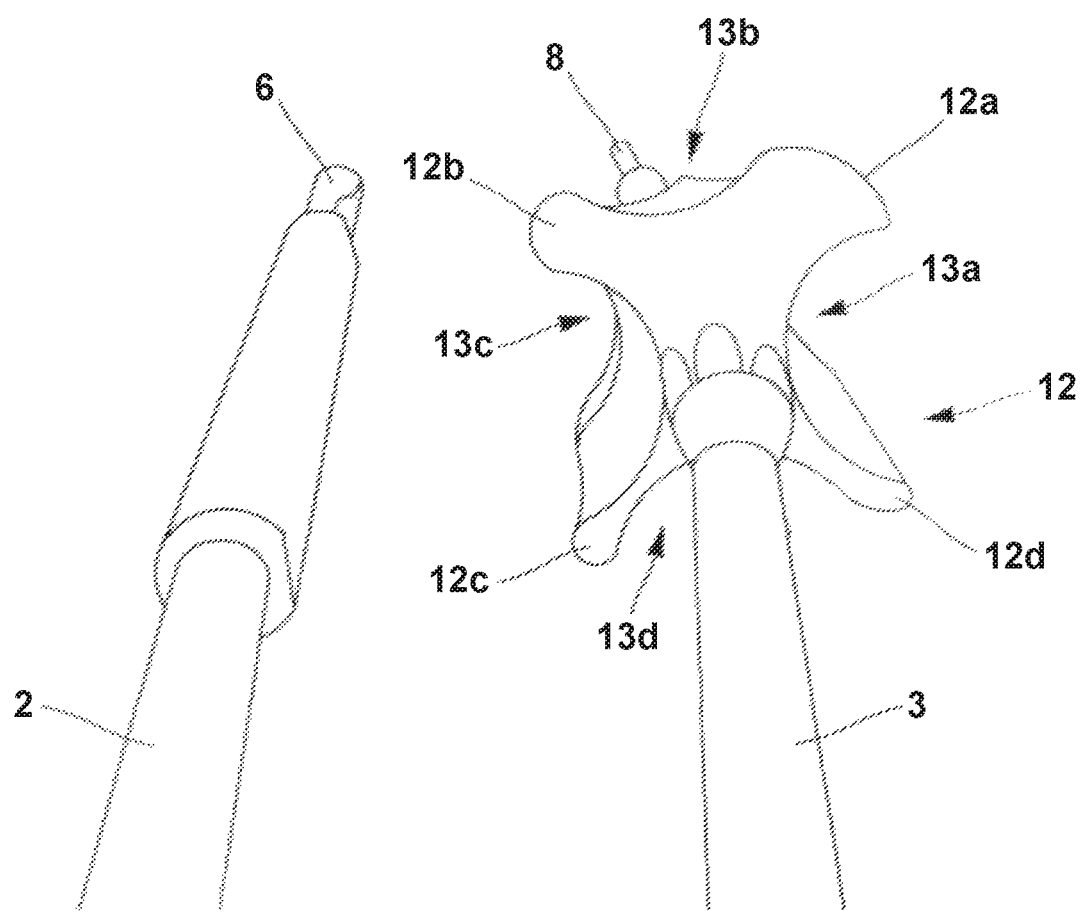
FIG. 8 shows a particularly advantageous configuration of the electrosurgical device according to the disclosure.

FIG. 8 shows a particularly advantageous configuration of the electrosurgical device 1. In this configuration, the second member 3 has means for rotating the second electrode 8 in the form of a rosette element 12, having four wings 12a, 12b, 12c, 12d and defining four recesses 13a, 13b, 13c, 13d for receiving the first member 2 when the two members 2, 3 are brought together. The wings and the contiguous recesses are separated from each other by an angular opening of 90°. The rosette element is free to rotate about an axis substantially defined by the longitudinal axis of the second member 3, and rotates the second electrode 8. This rotation movement is easily performed by the surgeon by acting on one of the wings 12a, 12b, 12c, 12d when the two members 2, 3 are not brought together, during surgery, to place the second electrode in a required orientation. The splayed form of the recesses 13a, 13b, 13c, 13d constitutes the means for guiding the first and second members 3 when the two members 2, 3 of the device 1 are brought together. The bottom of each recess 13a, 13b, 13c, 13d also constitutes a stop for the second member 2 when the two members 2, 3 are brought together. The position of the bottom in each recess and, therefore, the depth of each recess, can be chosen so as to position the second electrode 8 at a chosen distance from the first electrode 6 when the two members 2, 3 are brought together and placed in abutment. This distance may be different depending on the chosen orientation of the second electrode 8.

The multifunctional electrosurgical device 1 can be provided with one or more control switches, for example, disposed on one of its members 2, 3, to connect the electrodes 6, 8 to the generator 5 and to start up the device 1. Alternatively, the control switch or switches may be provided on the generator 5 or on the electrical connection between the generator 5 and the device 1. It may also be a case of one or more control switches on the floor that the surgeon can switch with his foot during the operation. Apart from the starting up of the device 1, the switches may also make it possible to control the energy level or the waveform delivered by the generator 5.

However, the disclosure does not require the existence of a plurality of control switches since the surgeon can easily choose the energy density applied to the tissues by modifying the extent of the contact surface of one or both electrodes 6, 8 with the tissues, as will be detailed in relation to the description of FIGS. 3 to 7.

The disclosure also relates to a method for treating biological tissues and, in particular, an incision and/or a cauterizing, comprising the following steps:

moving one toward the other, the first electrode 6 having a concave cross-section of a first member 2 and a second electrode 8 of a second member 3 of the multifunctional electrosurgical device 1 so as to partly house the second electrode 8 in the concavity of the first electrode 6 and to put the second electrode 8 projecting from the first electrode 6;

forming a first electrical contact between the tissues and an external surface of the first electrode 6 of the first member 2;

forming a second electrical contact between the tissues and the second electrode 8 of the second member 3;

circulating energy in the tissues between the first electrical contact and the second electrical contact in order to carry out the treatment.

The first three steps of forming the electrical contacts and moving the electrodes 6, 8 may be carried out in any order or even simultaneously.

The step of moving one of the electrodes 6, 8 toward the other makes it possible to make the second electrode 8 project vis-à-vis the first electrode 6, in particular, during an incision.

The movement of the first electrode 6 and of the second electrode 8 one toward the other is obtained by rotation about the articulation pivot 4 of the first member 2 and of the second member 3.

Preferentially, the second electrical contact is formed between the tissues and the projecting part of the second electrode 8.

The first embodiment of the treatment method relates to a method of incision by pressure. In this first mode, the first electrical contact is made on the external surface of the first electrode 6. The second electrical contact is made on the edge of the second electrode 8, in the form of a blade, at its projecting end. This configuration of the device is shown in FIG. 3. In this figure, the device 1 is moved in the direction of the arrow, and the tissues that have been travelled through by the device 1 and incised are shown in hatched form.

If necessary, this first embodiment may require a prior step of orientating the second electrode 8 by rotating this electrode about an axis substantially longitudinal to the second member 3, in order to ensure that the second electrical contact does indeed take place on the edge of the second electrode 8.

The second electrical contact takes place in this embodiment on a surface at one point, reduced with the tissues. Consequently, the energy deposited at the second electrical contact and/or circulating in the tissues between the first electrical contact and the second electrical contact has a high density, leading to the incision of the tissues. In this regard, this first embodiment is not limited to a second electrode 8 having an end in the form of a blade, and any electrode 8 having an end providing a punctiform or almost punctiform electrical contact is suitable. It may be a case, for example, of an electrode 8 having an end in the form of a needle.

In this embodiment, the method may also comprise a supplementary step of moving the first and second electrical contacts over the tissues during the operation in order to form the incision along a chosen length and path. This movement is obtained by moving the multifunctional electrosurgical device 1 in guided contact over the tissues in, for example, the direction indicated by the arrow in FIG. 3

An alternative to this first embodiment is present in FIG. 4 in which the device is substantially turned through 180° with respect to the previous embodiment. In this alternative, the first electrical contact is made on the first electrode 6, at the flanks 11a, 11b of the concavity (in particular, visible in FIG. 2). The second contact is made on the projecting edge of the second electrode 8. The linear contact surface between the second electrode 8 and the tissues extends over a portion of the edge of the electrode 8, which makes it possible to incise the tissues over a greater length without necessarily moving the device 1. This alternative also makes it possible to form deep incisions, in particular, when the energy level delivered by the generator is increased. In FIG. 4, the device 1 is moved in the direction of the arrow, and the tissues that have been travelled over by the device 1 and incised are shown in hatched form.

This alternative is not limited to a second electrode 8 having an end in the form of a blade. The electrode 8 may, in particular, have an end in the form of a needle.

A second embodiment of the treatment method relates to a method of incising by gripping. In this second mode, the tissues to be treated are first gripped between the first electrode 6 and the second electrode 8 by means of the gripping elements 7, 9, during the step of moving these elements one toward the other.

As in the first embodiment, and if necessary, a prior step of orienting the second electrode 8 may be provided.

As shown in FIG. 5, the first contact can be achieved between the tissues and the first electrode 6, in particular, on the external surface, and the second electrical contact can be achieved between the tissues and the edge of the second electrode 8.

Similarly to the previous embodiment, the second contact takes place on a smaller surface area with the tissues at the second electrode, punctiform or linear, giving rise to an energy density in the tissues sufficient for incision thereof. This embodiment is also compatible with a second electrode 8 having an end in the form of a needle.

A third embodiment of the treatment method relates to a method of pressure cauterization. This method is differentiated from the first embodiment of the treatment method in that the second electrical contact between the tissues and the second electrode 8 takes place on the flat of the second electrode 8. For this purpose, the device 1 is turned through 90° with respect to the first embodiment. The first electrical contact is achieved between the tissues and a flank 11a, 11b of the first electrode 6. This arrangement is shown in FIG. 6. In this figure, the device 1 is moved in the direction of the arrow.

If necessary, this third embodiment may require a prior step of orienting the second electrode 8 in order to ensure that the second electrical contact does indeed take place on its flat side.

The second electrical contact takes place with the tissues over a large surface area, on the projecting part of the second electrode 8. Consequently, the energy deposited at the second electrode 8 and/or circulating between the first electrical contact and the second electrical contact has a low density, insufficient to cause an incision, and leading to treatment by cauterization.

Figure 7:
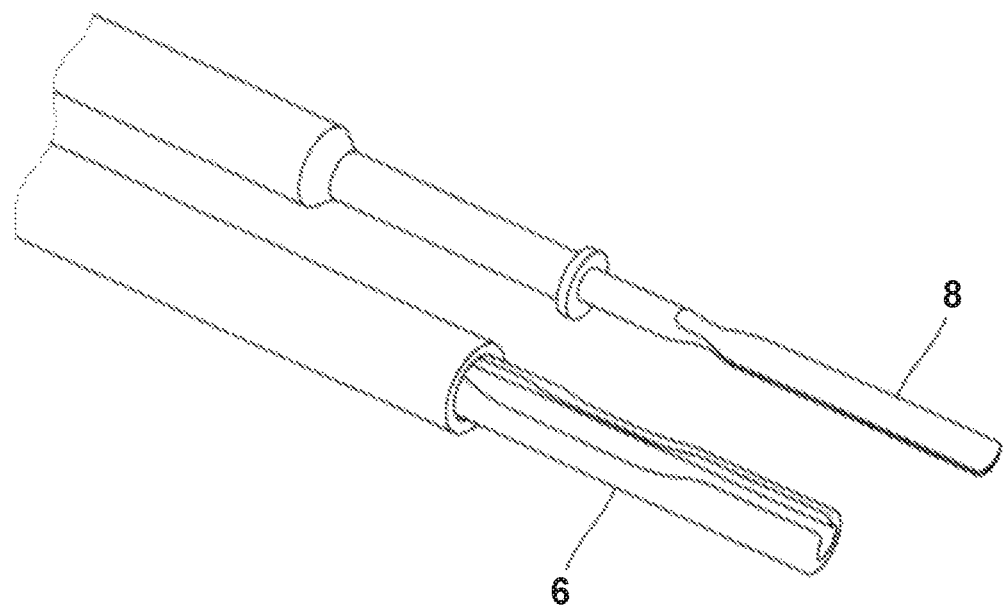
FIG. 7 shows the arrangement of the device of the disclosure for gripping cauterizing treatment.

A fourth embodiment of the treatment method relates to a method of cauterizing by gripping. This method is differentiated from the second embodiment of the treatment method in that the second electrical contact between the tissues and the second electrode 8 takes place on the flat of the electrode 8. This arrangement is shown in FIG. 7. If necessary, this fourth embodiment may require a prior step of orienting the second electrode in order to ensure that the second electrical contact does indeed take place on the flat of the second electrode.

Similarly to the third embodiment, the second electrical contact takes place with the tissues over a large surface area. Consequently, the energy deposited at the second electrode 8 and/or circulating between the first electrical contact and the second electrical contact has low density, insufficient to cause an incision, and leading to treatment by cauterization.

The surgeon may, during the same operation, alternate the deployment of the embodiments described above, in an uninterrupted manner and with a single device. He is also capable of proceeding with incision and cauterization operations, changing from one embodiment to the other, without needing, during the operation, to adjust the energy level and/or the waveform delivered by the generator 5.

According to another aspect, the disclosure, therefore, relates to a method for treating biological tissues, comprising the following steps:
  performing a first treatment of the tissues using a multifunctional electrosurgical device 1 connected to a generator 5;
  modifying, by rotation about its longitudinal axis, the orientation of the device 1 or of a part of this device 1;
  and performing a second treatment by means of the device 1.

The first and second treatments are, in particular, included in the list formed by an incision or a cauterization. Advantageously, the second treatment is different from the first.

Preferentially, the second treatment is performed without modifying the energy level and/or waveform delivered by the generator, with respect to the first treatment.

By way of example, the first treatment may be a pressure incision of the tissues, formed according to the first embodiment of the disclosure and shown in FIG. 3. In the following step, the device is entirely rotated through 90° in order to establish the electrical contacts with the tissues in the configuration of the third embodiment of the disclosure illustrated by FIG. 6. In the following step, and without modifying the energy level and/or waveform delivered by the generator, a pressure cauterization treatment is carried out in accordance with this third embodiment. Naturally, it is possible to reverse the two treatments carried out; that is to say, to carry out pressure cauterization during the first step and followed by a pressure incision in a subsequent step.

In a second example, the first treatment may be an incision treatment by gripping the tissues according to the second embodiment of the disclosure, shown in FIG. 5. In the following step, the second electrode is rotated through 90° in order to establish the electrical contacts with the tissues according to the configuration of the fourth embodiment of the disclosure, as illustrated by FIG. 7. In the following step, and without modifying the energy level and/or waveform delivered by the generator, a cauterization treatment by gripping is carried out in accordance with this fourth embodiment. Naturally, it is possible to reverse the two treatments carried out; that is to say, to carry out gripping cauterization during the first step and followed by a gripping incision in a subsequent step.

Naturally, the disclosure is not limited to the embodiments described and variant embodiments can be made thereto without departing from the scope of the disclosure as defined by the claims.

Thus, although it is described that one of the benefits of the disclosure lies in the possibility of carrying out varied treatments without necessarily modifying the energy level and/or the waveform delivered by the generator; the disclosure may entirely be implemented by modifying these parameters if the surgeon finds an advantage therein. For this purpose, the device 1 may be provided with a plurality of control switches, as described previously.

The invention claimed is:

1. A multi-purpose electrosurgical device for treating biological tissues, comprising a first member comprising at a front end thereof a first electrode to form a first electrical contact with the biological tissues and a second member consisting of a single second electrode connected to a gripping element, the single second electrode forming a front end of the second member, to form a second electrical contact with the biological tissues, the first and second members being connected by an articulation pivot making it possible to bring the members closer to and further away from one another; the first electrode having a concave cross-section defining a concavity having an internal surface able to partly house the second electrode, the first electrode having external flanks defining an external surface complementary to the internal surface of the concavity, and, when the two members are brought together, in a pressure mode such that no tissue is gripped between the first electrode and the second electrode, an end of the second electrode is longer than an end of the first electrode to make the second electrode project from the first electrode, a longitudinal axis of the first electrode and a longitudinal axis of the second electrode are not parallel to one another, and the external surface of the first electrode that faces away from the second electrode and a projecting part of the second electrode are configured to deliver energy to the biological tissues therebetween, wherein the second electrode rotates about an axis substantially defined by a longitudinal axis of the second member, a device for rotating the second electrode comprises a rosette element with wings and contiguous recesses separated from each other by an angular opening of 90°, and wherein a bottom of each recess constitutes a stop for the second member when the two members are brought together.

2. The multi-purpose electrosurgical device according to claim 1, wherein the second electrode is not entirely housed in the concavity of the first electrode when the two members are brought together, so that the second electrode is higher than the edges of this concavity.

3. The multi-purpose electrosurgical device according to claim 1, wherein the concave cross-section is a portion of a circle.

4. The multi-purpose electrosurgical device according to claim 1, wherein the end of the second electrode has a form of a blade.

5. The multi-purpose electrosurgical device according to claim 1, wherein the end of the second electrode has a form of a needle.

6. The multi-purpose electrosurgical device according to claim 4, wherein the second electrode in the form of the blade is oriented so that an edge of the blade is housed in the first electrode with a concave cross-section, when the two members are brought together.

7. The multi-purpose electrosurgical device according to claim 1, wherein the electrodes are assembled on gripping elements interchangeably.

8. The multi-purpose electrosurgical device according to claim 1, wherein a splayed form of the recesses are configured to guide the first and second members when the two members of the device are brought together.

9. The multi-purpose electrosurgical device according to claim 1, wherein the depth of each recess is chosen so as to position the second electrode at a chosen distance from the first electrode when the two members are brought together and placed in abutment, the chosen distance being different depending on the chosen orientation of the second electrode.

* * * * *